United States Patent [19]

O'Dell et al.

[11] 4,400,820
[45] Aug. 23, 1983

[54] AXIAL TOMOGRAPHY HEAD HOLDER

[75] Inventors: William R. O'Dell, Milwaukee; Christine M. Fletcher, Madison, both of Wis.

[73] Assignee: General Electric Company, Schenectady, N.Y.

[21] Appl. No.: 430,149

[22] Filed: Sep. 30, 1982

[51] Int. Cl.³ .................... A61B 6/00; A61B 19/00; A61F 13/00
[52] U.S. Cl. .................... 378/209; 378/17; 378/20; 128/133; 128/134
[58] Field of Search .................... 378/4, 20, 208, 209, 378/17; 128/133, 134, 135

[56] References Cited

U.S. PATENT DOCUMENTS

| | | | |
|---|---|---|---|
| 3,449,570 | 6/1969 | Kok | 378/209 |
| 3,897,777 | 8/1975 | Morrison | 378/208 |
| 4,058,112 | 11/1977 | Johnson | 128/133 |
| 4,297,994 | 11/1981 | Bashaw | 128/133 |

Primary Examiner—Eugene La Roche
Assistant Examiner—T. N. Grigsby
Attorney, Agent, or Firm—Wheeler, House, Fuller & Hohenfeldt

[57] ABSTRACT

A head holder for an X-ray subject uses a rigid U-shaped receptacle having an angulated cervical extension that fastens to a patient supporting cradle. A head restraint sheet that may be preformed to a U-shape has a tie-down strap fastened to it is wrapped about the bottom and sides of a flexible foam preformed U-shaped liner that has notches for accommodating the subject's ears. The sheet and liner are deposited in the U-shaped rigid receptacle with the head of the subject in the liner and the strap ends crossed over the forehead and attached to "Velcro" pile that is fixed on the outside of the receptacle. The resilient foam liner and flexible sheet act as a pressure feedback system which restores a head to its initial relaxed position if the head has moved. A wedge is inserted between the flexible sheet and receptacle bottom to tilt the head of the subject.

15 Claims, 9 Drawing Figures

AXIAL TOMOGRAPHY HEAD HOLDER

BACKGROUND OF THE INVENTION

This invention relates to a holder for stabilizing the head of a subject who is prepared for undergoing a cranial X-ray examination. The holder is especially useful for computed axial tomography cranial examinations and will be described primarily in relation to that procedure.

As is well known, computed tomography apparatus is used for obtaining X-ray attenuation data from a thin body layer for the purpose of enabling reconstruction of an X-ray image that allows the layer to be viewed in an axial perspective. Computed tomography apparatus comprises an X-ray tube located on one side of a human body undergoing an X-ray scan and a multiple-element X-ray detector located on the other side of the body. The X-ray tube and detector are mounted on a gantry and are driven rotationally about a horizontal longitudinal axis so the tube and detector orbit the X-ray examination subject jointly. The X-ray beam emitted from the focal spot of the X-ray tube is collimated into a thin diverging or fan-shaped beam whose thickness corresponds with the thickness of the layer in the body being scanned. A common mounting for the X-ray tube and multiple-element detector is part of the gantry which permits the mounting and, hence, the rotational plane of the tube and detector to be tilted about a laterally extending horizontal axis to which the longitudinal axis is perpendicular. This permits making a scan and obtaining X-ray attenuation data for an image of a transfer slice or layer of the body which is at an angle relative to the vertical and to the longitudinal axis. It is necessary for the gantry to be constructed so the intersection point of the longitudinal and transverse axes do not shift in any direction when the rotational plane is tilted. The intersection point is called the isocenter. The longitudinal axis projects through the isocenter. A computed tomography gantry is described in U.S. Pat. No. 4,112,303 which is owned by the assignee of this application.

Typically, to make a cranial axial tomographic examination, the subject is supported in a supine position on an elongated X-ray transmissive cradle. The cradle is translatable so it overhangs the base on which it is mounted in cantilever fashion. A head holder or restraint is mounted near the end of the cradle for the purpose of stabilizing and maintaining the subject's head in a fixed position during the relatively long time which is required for scanning several adjacent cranial cross-sections or layers. It is important for the head of the subject to not move during the scan of a layer and that the head be in the identical position for each one of the successive scans. By way of example, it is usually desired that both optic nerves appear simultaneously in one of the axial perspective layers. The geometrical relationship of the subject's head to the plane of the fan-shaped X-ray beam is usually determined before the final tomographic scan is made. In other words, the subject is pre-positioned so that when the scan is made there is reasonable certainty that both optic nerves will be in view. A change in the subject's position of as little as 2 mm can then defeat the objective of imaging both optic nerves fully in the same axial view.

Some cranial X-ray studies may require the head of the subject to be in exactly the same position at the end of as much as forty minutes as at the beginning. Typically, the cranial study procedure involves making a computed projection radiograph which can be viewed to determine where and at what angle the fan-shaped scanning beam should be directed relative to the longitudinal axis of the subject's head. Minutes are often required in the decision-making process. As many as twenty layers may be scanned subsequently for obtaining the axial views. Although the cycle time per scan may be well under one minute, additional time may be consumed by waiting for an X-ray opaque medium which has been injected in the blood vessels to arrive at the proper place in the brain or cranium for getting the desired diagnostic information. Head holders that were available before the holder to be described later was invented have been found to be incapable of keeping the head of the subject in a precisely fixed position over a long period of time and are incapable of restoring the head to the predetermined desired position if there has been some movement over the long period.

SUMMARY OF THE INVENTION

The new head holder is distinguished by its ability to induce the subject to relax and achieve a head position that can be comfortably maintained over a long period of time. The new head holder comprises a U-shaped X-ray transmissive receptacle (sometimes called a bucket) which has a liner or insert that is pre-formed and maintains a substantial U-shape and registers in the receptacle. The liner is composed of a resilient foam material, such as open cell urethane foam. When the head of the subject is placed within the U-shaped space in the foam liner and the liner is residing in the receptacle which is anchored to the X-ray table top and the head is strapped into the receptacle, the head will cause the resilient liner to conform and the subject can relax in that position. When the head is fixed in this position in the holder by using straps, the body is in its most relaxed position and the foam liner is somewhat compressed. The skin is movable over the skull so complete immobilization is impossible even if the head were strapped quite tightly. Moreover, it is impossible for the subject to maintain an absolutely fixed position. If the head moves voluntarily or involuntarily, the grip of a strap running tightly over the skin on the forehead puts the skin in tension, a condition which is felt by the subject and which tends to induce the subject to turn the head slightly back to the position where no skin tension is felt. This is the identical position the subject was in when initially strapped. Moreover, when the subject's head moves slightly, a greater resilient force is developed on the area of the foam liner that is increasingly compressed by the movement such that the increased resilient force will restore the head to its initial position.

The new head holder, particularly the receptacle, is configured in such manner that it provides support behind the neck at an angle that corresponds to the natural angle of the cervical spine when a subject in in the holder. Moreover, the holder receptacle is formed in a manner which allows the head to extend beyond the end of the cantilever X-ray subject supporting cradle without having the shoulders of the subject interfere with proper longitudinal positioning of the head.

Another feature of the invention is that the resilient liner can be used as a head holer by itself, that is, without using the more rigid receptacle. This practice is one that may have to be followed in those cases where the subject may be uncooperative or violent as head trauma cases sometimes are and where further damage may result from angulation the cervical region as would occur if the rigid pre-formed receptacle were used.

The new head holder is also designed in such fashion that it does not block sound passage to the subject's ears so the subject can be conversed with during the examination.

Briefly stated, the new head holder comprises a rigid generally U-shaped X-ray transmissive receptacle or bucket that has a concave bottom wall and laterally spaced apart integral side walls. Means are provided for mounting the receptacle to a body supporting cradle. A head restraint means comprising a thin sheet of flexible X-ray transmissive material, which can be performed into a U-shaped sheet desirably, is inserted in the U-shaped space in the receptacle and conforms with the contour of the space. Straps are fastened to the head restraint means and have free ends extending beyond its edges for being wrapped over the head of the subject and at least partially around the receptacle to restrain the head. A resilient foam liner is, however, first interposed between the thin head restraint means and the subject's head and the liner is sufficiently rigid to maintain its shape and sufficiently resilient to always restore the head to the original position in which it was fixed. Wedges are provided for being interposed between the head in the liner and the rigid receptacle to tilt the head down or up about a virtual tilt axis that coincides with an imaginary line between the external auditory canals of the left and right ears.

A more detailed description of a preferred embodiment of the new head holder will now be set forth in reference to the accompanying drawings.

DESCRIPTION OF A PREFERRED EMBODIMENT

Figure 1:
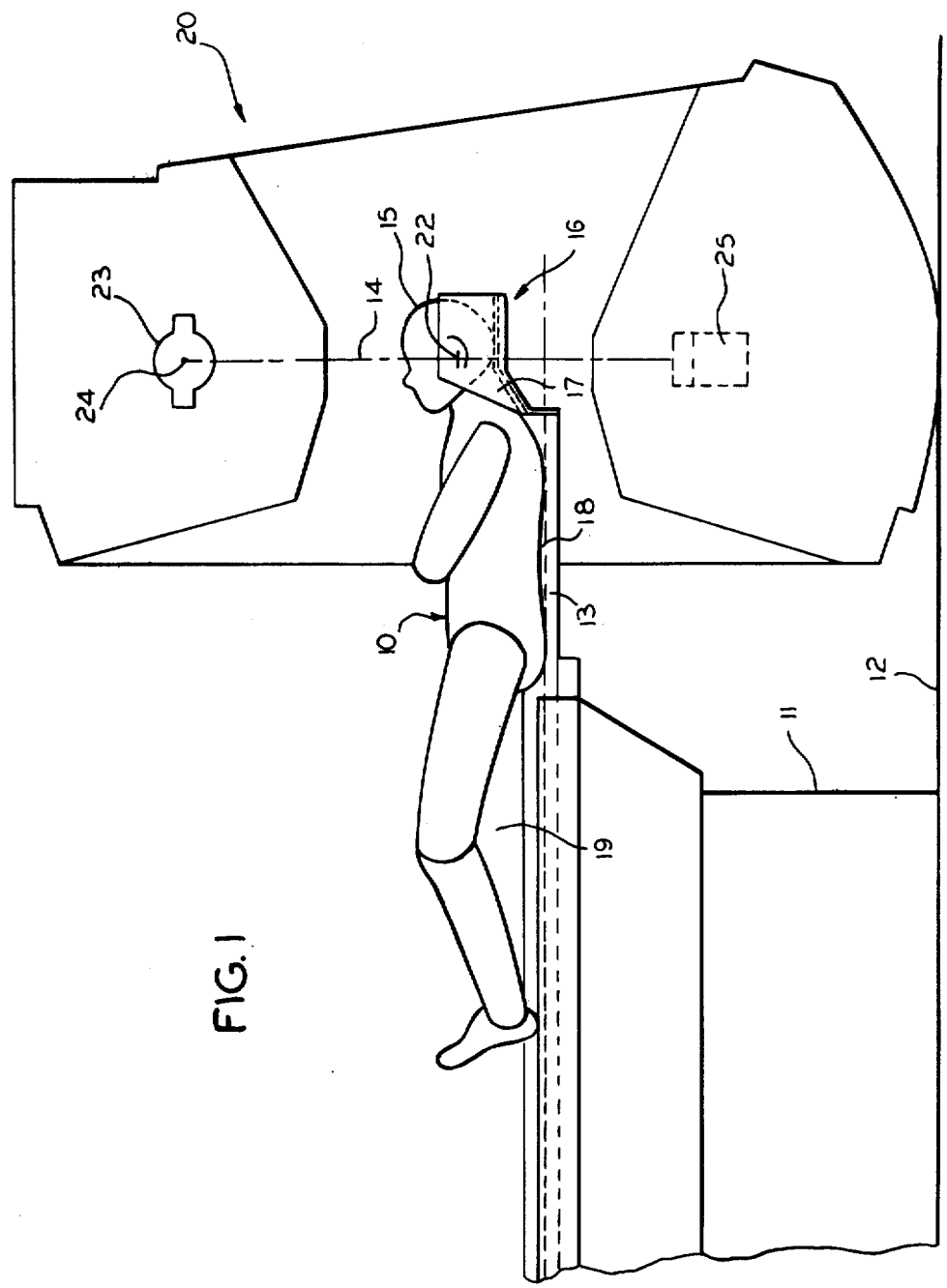
FIG. 1 is a diagrammatic side elevation view showing a human subject supported on a longitudinally movable cantilever cradle wherein the subject's head is advanced into the X-ray beam path in a computed tomography scanner and wherein the head is supported in the new head holder.

Referring to the FIG. 1 schematic view, the human subject who is prepared for cranial axial tomography is indicated by the reference numeral 10. There is an X-ray table base 11 standing on the floor 12. The subject is supported on an X-ray transmissive cradle 13. The cradle 13 can be translated inwardly or outwardly, that is, to the left and right as viewed in FIG. 1 for positioning the head of the subject in the plane of the fan-shaped X-ray beam whose central ray, looking at the beam from the edge is marked 14. The subject's head 15 is presently residing in the new head holder which is shown in outline in FIG. 1 and is designated generally by the reference numeral 16. The cervix 17 of the subject and the cervical spine therein are at their normal angle which, in a practical case is achieved by supporting the back of the subject in region 18 with a thin pillow, not shown and by having a pillow, not shown, inserted in the region 19 below the knees to bend them upwardly and relax them and allow the spine to be in an undeformed attitude as depicted in FIG. 1. A typical X-ray subject supporting cradle 13 to which the new head holder 16 may be attached is depicted in substantial detail in U.S. Pat. No. 4,262,204 which is assigned to the assignee of this application.

Still referring to FIG. 1, the computed tomography gantry is designated generally by the reference numeral 20 and is shown diagrammatically. The gantry comprises a frame 21 that can tilt either left or right as viewed in FIG. 1 about a virtual horizontal axis or isocenter that is marked 22. The head of the subject is positioned so that the external ear canal is substantially coincident with the isocenter. Gantry 21 contains a diagrammatically illustrated X-ray tube 23 that has a focal spot 24 from which the X-ray beam is emitted toward the subject's head. The collimator for collimating the X-ray beam into a thin fan-shaped beam has been omitted from the diagram. The X-ray beam 14 penetrates the subject's head and is intercepted by a multiple cell X-ray detector 25 whose one end is symbolized by a dashed line rectangle in FIG. 1. As is known, in computed axial tomography scanners, the X-ray tube 23 and detector 25 are mounted on a turrent that rotates in the gantry and causes the X-ray tube and detector to orbit te subject's body jointly during an X-ray beam scan of a layer in the body or a part thereof such as the head. The X-ray tube and detector orbit about a longitudinal axis that intersects the transverse axis on which the gantry is tilted to form the isocenter 22. As will be evident later, the new holder permits the head to be tilted forward or backward by using some wedges that are to be described. When the head is tilted with the wedges it rotates about a virtual center which is coincident with the external auditory canal. The technician performing the examinations uses an imaginary line drawn from the ear canal or virtual center to the edge of the eye as a reference line for determining the tilt angle of the head. A gantry 20 that is suitable for performing cranial axial tomography is illustrated in U.S. Pat. No. 4,112,303 and a typical multi-cell X-ray detector 25 is illustrated in U.S. Pat. No. 4,119,853. Both patents are assigned to the assignee of this application.

The manner in which visible images of body layers that have been subjected to X-ray beam scans are formed using signals developed in the X-ray detector 25 is well known and need not be described. For present purposes it is only necessary to recognize that the cranial examination procedure requires obtaining axial images of several layers in the head in one mode where the X-ray beam axis is at an angle from vertical or directly vertical or in another mode where the head is tilted forwardly or backwardly relative to the vertical or tilted fan-shaped X-ray beam.

Figure 2:
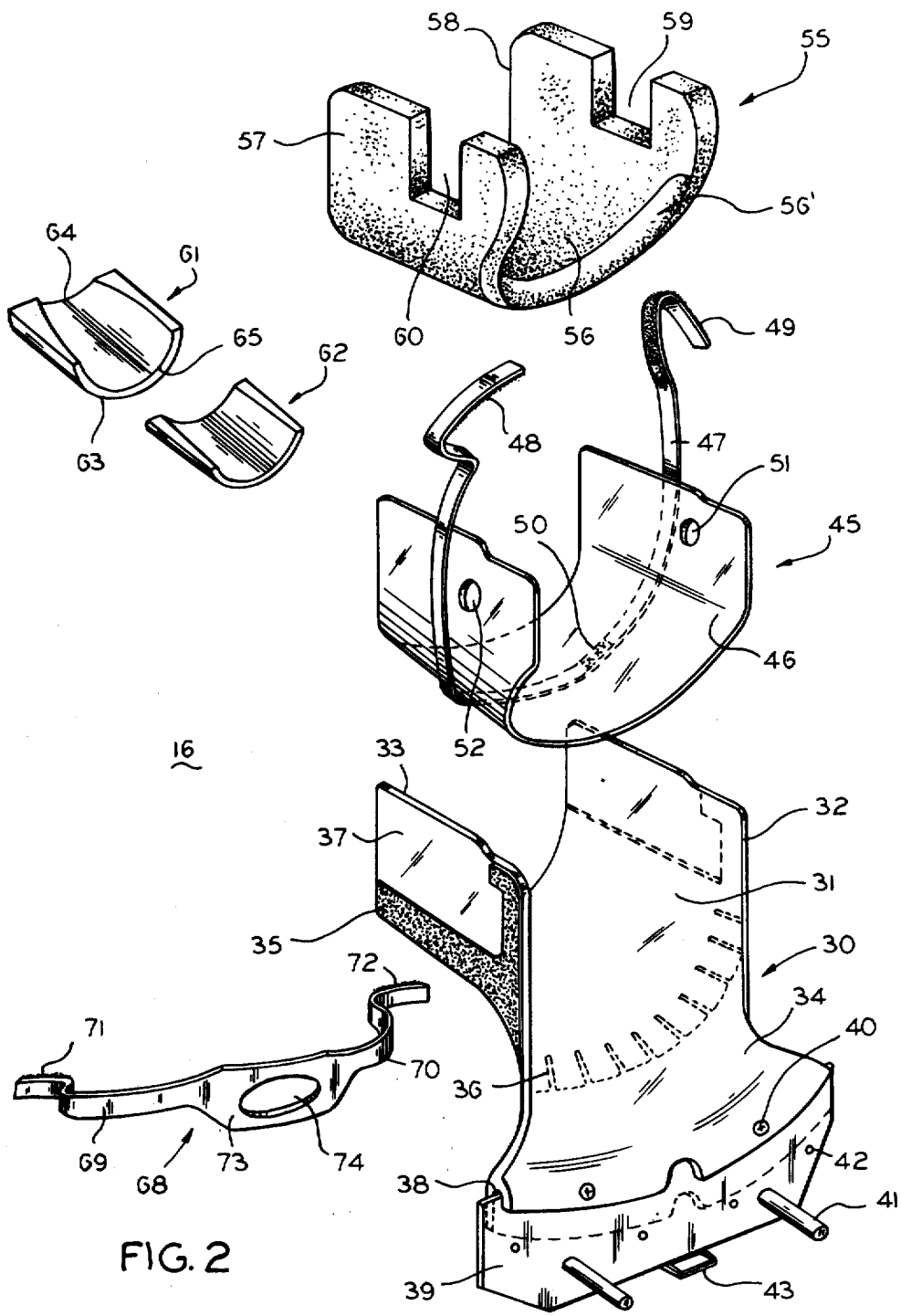
FIG. 2 is an exploded perspective view of the head holder.

The parts of the new head holder 16 are shown in the relationship in which they are assembled in the FIG. 2 exploded view to which attention is now invited. The holder comprises a rigid bucket or receptacle that is generally designated by the reference numeral 30. The receptacle is generally U-shaped and is molded in a single piece out of a material that has low X-ray attenuation properties. In the commercial embodiment, the material is polycarbonate resin which is obtainable from General Electric Company under its trademark "LEXAN." The U-shaped receptacle has a curved or concave bottom wall 31 and upstanding parallel and laterally spaced apart side walls 32 and 33 which are integral with concave bottom wall 31. Thus, side walls 32 and 33 in conjunction with concave bottom wall 31 of the receptacle form the U-shaped configuration or space in which the head of the subject and some other components to be described can be accommodated. Confluent and integral with bottom wall 31 there is an extension 34 of the receptacle. As will be evident in other FIGURES such as FIG. 6, the extension 34 is angulated downwardly from the bottom 31 of the receptacle and the angle is such as to conform to the angle of the cervical spine of a normal subject lying supine on the cradle 13. In FIG. 2, the outside of the receptacle 30 is coated in part with a sheet of pile material 35 which is part of a fastening means known by the trademark "Velcro." The pile sheet is split at its edge as indicated at 36 so it will lie smoothly against the bottom outside of the receptacle on which it is adhered. Note that there are clear transparent area such as the one marked 37 on the side walls of the receptacle which permit visualizing the external auditory canal of the subject who is being examined with the head in the head holder Receptacle 30 terminates beyond the angulated cervix supporting extension 34 in a grooved margin 38 which allows it to fit onto the upper edge of an adapter plate 39. The receptacle may be seucred to the adapter plate by any suitable means such as by screws 40. The adapter plate 39 is for facilitating coupling the head holder receptacle 31 to the end of the cradle 13. To make it easy to fit the adapter to the cradle and to assure that it will be in a reproducible position, the adapter is provided with at least two dowel pins 41 that fit into suitable holes, not shown, in the end of the cradle. Screw holes 42 are for screws that are used to secure the adapter for the free end of the cradle. There is also a fastening device 43 for holding the head holder temporarily while the screws through holes 42 are being secured.

Referring further to FIG. 2, the head holder assembly includes a head restraint means that is generally designated by the numeral 45. The head restraint means may comprise a flexible sheet 46 of X-ray transmissive material such as a transparent synthetic resin material that can be readily bent so it will conform with the U-shaped region of the head holder which is defined by its concave bottom wall 31 and its laterally spaced apart side walls 32 and 33. It is preferable to preform the thin plastic head restraint 46 sheet into a U-shaped configuration so it has a permanent set and will not have a tendency to spring open and lay flat as a simple plastic sheet will do. The head restraint member 46 will, however, be called a sheet for the sake of brevity. The head restraint sheet 45 is provided with a strap 47 which may be vinyl, by way of example and not limitation. This strap is otherwise known as a forehead strap. The ends of the strap have a band of hook material 48 and 49 or Velcro hook material adhered to them. In the preferred embodiment, the strap 47 is sewed at its center or intermediate its ends to the outside of the sheet 46. The region in which the sewing is done is marked 50. When the subject's head is in the head holder the free ends of the strap are wrapped around in opposite directions or crossed over the subject's forehead and the ends 48 and 49 that contain the hooks are engaged with the pile 35 on the receptacle 30. The head restraint sheet 45 is also provided with a pair of holes 51 and 52 that will align with the subject's external auditory canals when the subject's head is in the holder.

Referring further to FIG. 2, the head holder assembly includes a liner or insert that is indicated generally by the reference numeral 55. The liner is preferably made from an open cell foam material such as urethane and the foam should have sufficient durometer for the liner to maintain the shape in which it appears in FIG. 2 when it is free standing and separated from the receptacle 30. The liner is spongy and resilient and has a tendency to restore its surfaces to their original shape when the surfaces are deformed by pressure that may be exerted by the head of the subject with which the liner directly interfaces which the head holder is in use. More specifically, the liner 55 is an integral member comprised of a curved or concave bottom wall 56 that is confluent with or integral with laterally spaced apart and parallel side walls 57 and 58. Each side wall has a notch such as those marked 59 and 60. These notches are for accommodating the subject's ears when the head is residing in liner 55 and the liner is at least partially surrounded by head restraint sheet 45 and the head is in the holder. It will be evident that the open tops on the notches 59 and 60 provide open-ended channels by which sound can travel to the ears even though the liner 55 and head restraint sheet 45 are occupied by the subject's head and the head is residing in the U-shaped receptacle 30. Note that the front edge of the insertable liner 55 has a bevel 56' which will follow the contour of the cervix or the back of the head and provide a better fit.

In FIG. 2, two wedges are shown and they are indicated generally by the numerals 61 and 62. Wedges 61 and 62 are for tilting the subject's head rearwardly or forwardly before the head is secured prior to an X-ray beam scanning sequence. Use of the wedges will be discussed in somewhat more detail later in reference to FIGS. 8–10, primarily. In FIG. 2 a typical wedge 61 is composed of a fairly high durometer closed cell synthetic resin foam by way of example and not limitation. The wedges are preferably somewhat pliable and resilient for the sake of comfort but not sufficiently resilient or compressible to significantly deform when subjected to the pressure exerted by the subject's head when the head is in the holder. Typical wedge 61 has a circular outside periphery 63 and is basically a split cylinder. The interior of the cylinder is tapered from the thick end 64 in the longitudinal direction to the thin end 65. The radius of curvature of the outside periphery 63 is substantially the same as the radius of curvature of the concave or curved bottom wall 31 of the rigid receptacle 30 so the wedges will nest in conformity with the contour of the bottom wall 31 of the receptacle 30.

FIG. 2 also shows a chin strap 68 that is used with the head holder. This strap may be vinyl or some other flexible material. It has two narrow free ends 69 and 70 which near their tips are provided with Velcro hook material 71 and 72 for engagement with the pile 35 on rigid receptacle 30. Chin strap 68 has a wider central region 73 in which there is a hole 74 into which the tip of the chin may extend for the purpose of augmenting stabilizing it and the head of the subject when the holder is in use.

Figure 5:
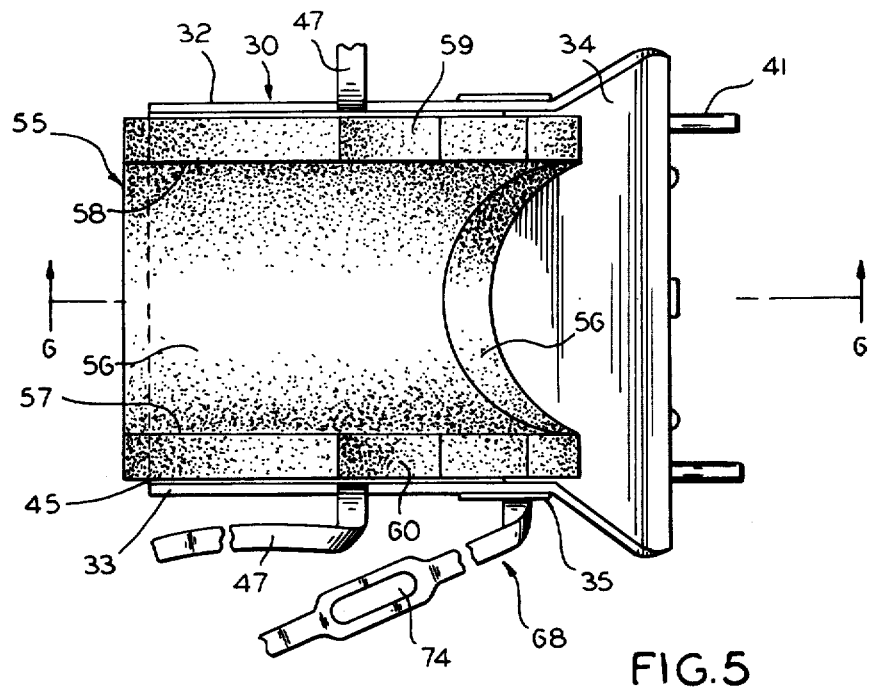
FIG. 5 is a plan view of the head holder detached from the subject supporting cradle.

A plan view of the assembled head holder is depicted in FIG. 5. The foam insert is bottomed in the U-shaped receptacle 30. The side walls 57 and 58 of the foam liner are interfaced with the thin preferably preformed into a U-shape plastic head restraining sheet 35 which is, in turn, interfaced with the side walls and bottom of the rigid receptacle 30. Thus, if the head of the subject, when residing in the foam insert 55, is moved, the resilient foam will deform under the compressive force and the liner will react against the receptacle through the head restraining sheet 35. The restoring force thus developed in the liner due to its resilience tends to return the subject's head to the exact position in which it was when it was strapped down with the forehead strap 47 and the chin strap 68. In other words, there is a pressure feedback system acting around the skull. If the subject shifts in the foam liner, the foam induces the head to go back to its relaxed position and, as mentioned earlier, wany stretching of the skin under the tight strap signals the subject to relax and let the resilient foam do the restoration. Thus, the plastic head restraining sheet provides an even circumferential pressure around the subject's skull, thereby providing rotational feedback to the subject. Generally in practice, the foam liner 55 is slipped onto the subject's head or deposited in the rigid receptacle 30 over the head restraining sheet 45 before the subject's head is in the receptacle to avoid hurting the subject.

Figure 6:
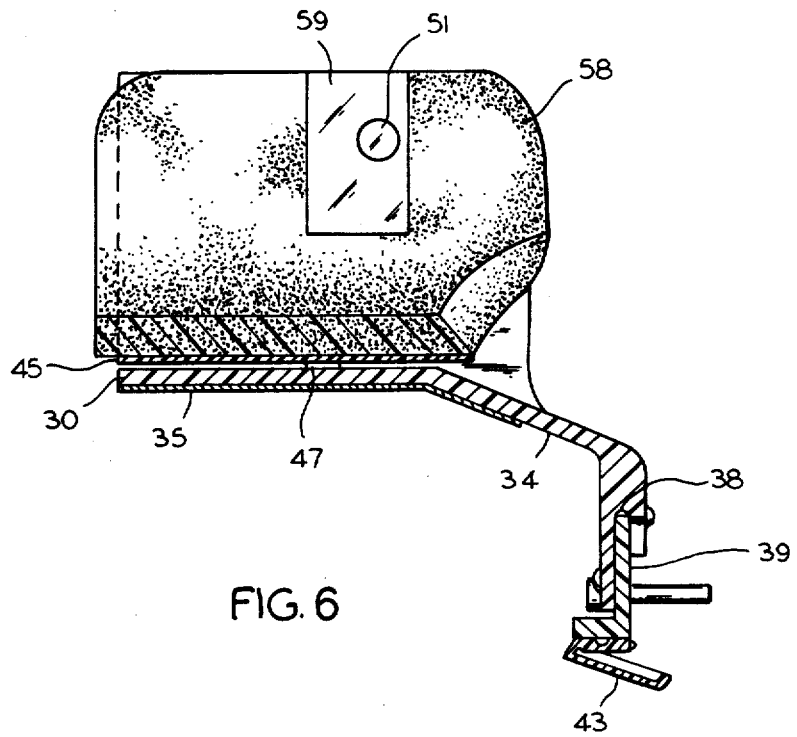
FIG. 6 is a vertical section taken on a line corresponding with 6—6 in FIG. 5.

The vertical section in FIG. 6 illustrates how the cervix region 34 of the rigid receptacle is angulated relative to the nominally longitudinally horizontal bottom of the receptacle 30. Note also in FIG. 6 that the ear hole 51 in the U-shaped head restraining sheet 45 aligns with the open-topped notch 59 or sound channel in the flexible foam insert wall 58.

Figure 3:
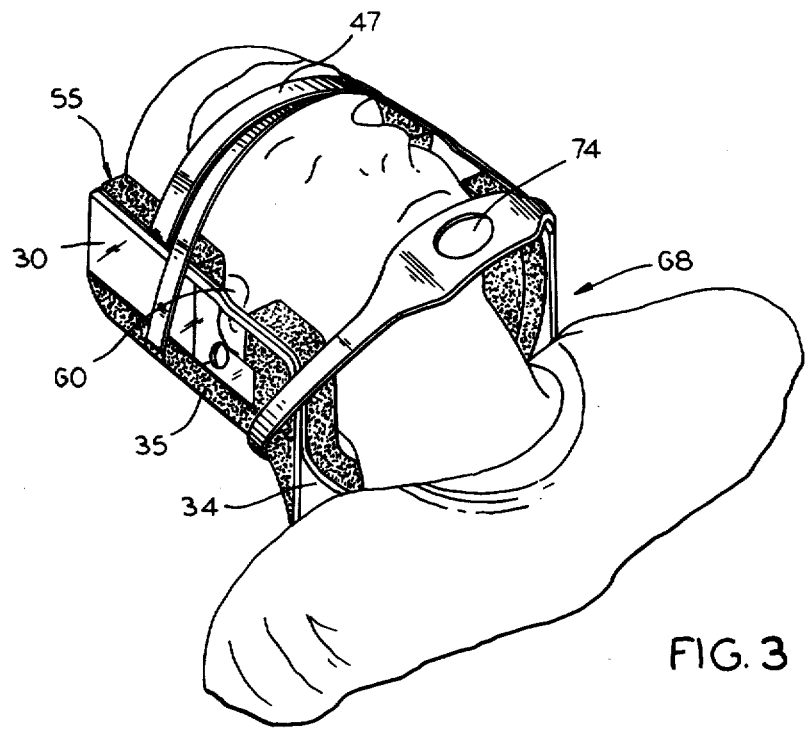
FIG. 3 is an enlarged perspective view of the head of a subject who is fastened in the head holder and ready for a tomographic examination.

FIG. 3 shows the head of the subject in the holder and ready for X-ray scanning. Opposite ends of the forehead strap 47 are crossed-over and wrapped over the subject's forehead and the ends of this strap having the Velcro hooks are engaged with the pile 35 on the outside of the rigid receptacle 30. The head is positioned rotationally by exerting tension on the opposite strap ends as they are being attached to the Velcro pile 35. The forehead strap 47 is easily angled or set in a longitudinal position on the forehead to fit different forehead slants or shapes. The ears of the subject are in the recesses such as the one marked 60 that are provided in the side walls of the foam insert liner 55. The chin strap 68 is laid over the chin and its ends having the Velcro hooks 71 and 72 are engaged with the pile 35 on the receptacle. The chin is protruding into the hole 74 in the chin strap to enhance stability. The angulated portion 34 of the receptacle is right behind the cervix of the subject and the shoulders of the subject are brought right up to the end of the holder. The commercial embodiment is designed so that the back of the head is about ten centimeters above the plane of the patient supporting cradle 13 so that the cervical spine can assume its natural angle for the average subject.

Figure 7:
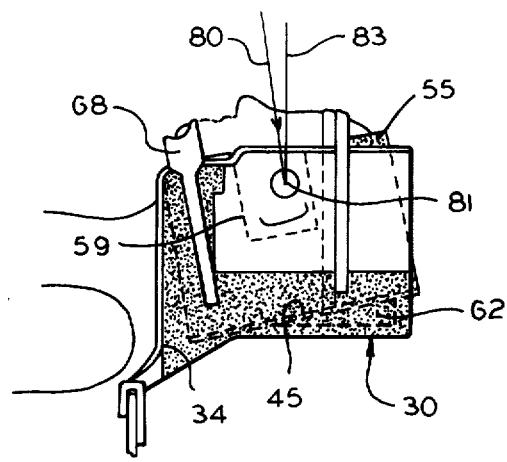
FIG. 7 shows the head of the subject in the new head holder wherein the head is tilted forward by means of a wedge of one size.

FIG. 7 is a diagram of a subject disposed in the head holder 16 for a very frequently used modality where the head is tilted slightly forward by reason of one of the less tapered closed cell foam wedges 62 having been inserted between the curved bottom of receptacle 30 and the outside bottom of the curved thin head restraint sheet 45. The exterior auditory canal is visible since the ear of the subject is residing in notch or recess 59 of foam liner 55 and the ear is behind the transparent wall of receptacle 30. Here the vertical line 83 is estimated by the radiologist with reference to the center 81 of the external auditory canal and the angle of tilt is determined by using the reference line 80 which is an imaginary line extending from center 81 to the corner of the eye. In accordance with the invention, inserting one of the wedges such as wedge 62 from the top of the patient's head caused rotation of the head about a virtual center which is the center 81 of the auditory canal so that there is only rotation and not translation of the head. If the tilt were made about the cervical region, the head would translate which is undesirable. The chin strap 68 has its ends secured to Velcro pile 35 and the forehead strap 47 ends are crossed over on the forehead and attached to the Velcro. The subject is asked to assume a natural relaxed position while straps are being fastened so as to impart an initial deformation to the foam liner 55 which will, by reason of its resiliency, always restore the subject's head to its initial position in case there has been some movement and the subject relaxes.

Figure 8:
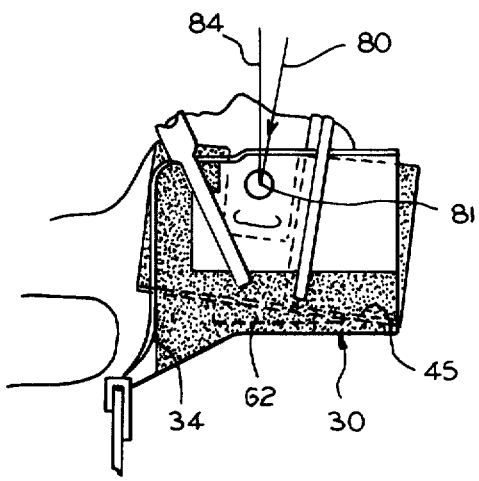
FIG. 8 shows the head in the holder and tilted backward where the same sized wedge is used as in FIG. 9.

In FIG. 8, the thinner of the two wedges 62 is inserted with its taper pointed toward the top of the subject's head in which case the head tilts rearwardly. Here again the examining technician determines the angle of tilt by estimating the angle between the reference line 80 between the auditory canal and corner of the eye and vertical line 84.

Figure 9:
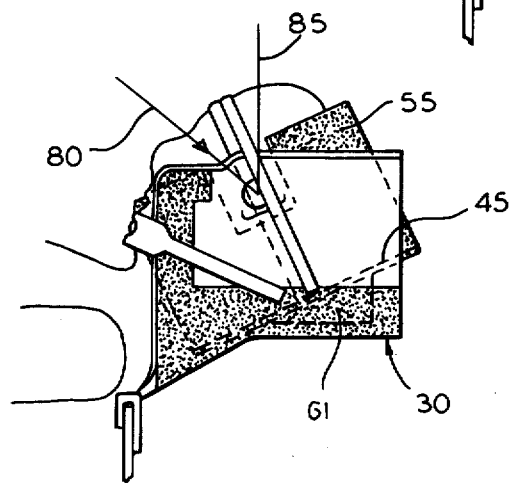
FIG. 9 shows the subject's head in the holder and tilted forward by a greater amount than in FIG. 7 by reason of using a larger wedge.

In FIG. 9, the larger or more tapered wedge 61 is used such as would be used for a kyphotic or elderly patient who has a so-called dowager's hump. The larger wedge supports the cervix in its natural attitude for this type of subject. The tilt angle is determined by estimating the angle between the reference line 80 and vertical line 85 as in the previous examples.

As indicated earlier, a computed projection radiograph is frequently made to provide an indication of where and at what angle the plane of the fan-shaped X-ray beam should have relative to the head of the subject. The computed projection radiograph is displayed on a television monitor, not shown, customarily so the radiologist or X-ray techinician can make a judgment as to the angle required for viewing the region of interest such as both optic nerves in the cranium. When the desired angle is determined, a wedge is inserted or not inserted as may be required.

Figure 4:
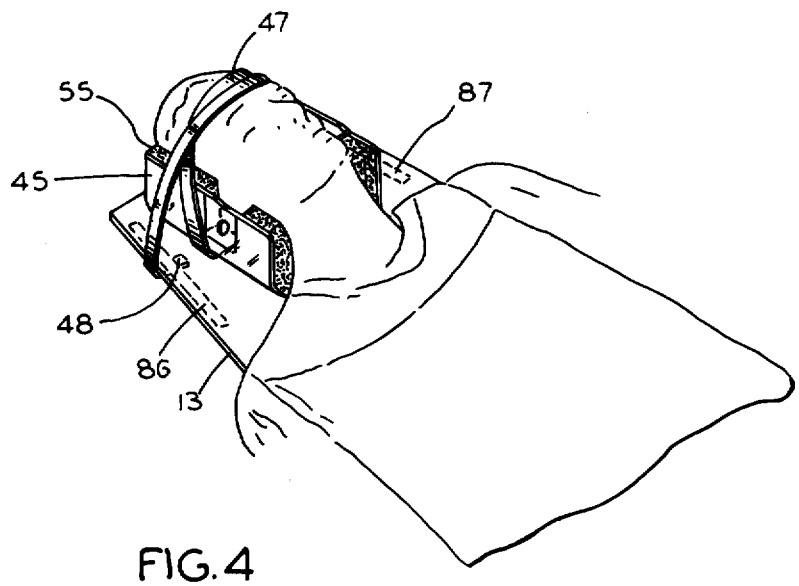
FIG. 4 shows a subject whose head is resting directly on the cantilever type cradle in which case the interior parts of the head holder are used and the receptacle which is part of the combination in the FIG. 2 and 3 embodiment is omitted.

As indicated earlier, some subjects may be uncooperative or so severely injured that it would be undesirable or impossible to let the cervix be supported on the angulated extension 34 of the rigid receptacle 30. FIG. 4 shows what is done in such cases. Here the head restraint sheet 45 is used with the resilient foam liner 55 nested therein. The forehead strap 47 is crossed over the forehead of the subject. Velcro pile material strips 86 and 87 are adhered to the bottom of the table top 13 on which the subject is supported. The Velcro hook containing ends such as the one marked 48 on the forehead strap 47 engage with the fixed pile strips 86 to hold the subject's head down. Here again, the subject's head is in a relaxed or neutral state when the holder assembly is tied down. The skin is held by the strap but the skull can turn under the skin by about one-half inch. There is an original deformation of the resilient foam liner 55 which will provide the restoring force to the original position of the head after the head has moved and the subject becomes relaxed again. If the skin becomes tensioned by skull rotation the subject signalled to relax so the resilient foam liner can do its work.

Although a preferred embodiment of the new holder has been described in detail, such description is intended to be illustrative rather than limiting, for the invention may be variously embodied and is to be limited only by the claims which follow.

We claim:

1. A holder for stabilizing the head of a subject lying on the cradle of an X-ray table, the holder comprising:
    a rigid generally U-shaped transmissive receptacle comprised of a longitudinally extending concave bottom wall and laterally spaced apart longitudinally extending side walls projecting, respectively, integrally from opposite sides of the bottom wall, said bottom wall and said side walls defining a U-shaped space that is wider than the head, and a concave extension projecting integrally from the bottom wall at an angle that corresponds generally to the angle of the cervical spine of the subject lying supine on said table top,
    means for mounting said receptacle to said cradle,
    head restraint means comprised of a sheet of X-ray transmissive material for being inserted in said U-shaped space in the receptacle in general conformity with the contour of said U-shaped space in the receptacle, and strap means fastened to said head restraint means and having free ends extending beyond its laterally opposite sides for being wrapped over the head of a subject and at least partially around the receptacle to restrain the head, and
    a unitary liner member composed of a flexible compressible material that is sufficiently rigid to maintain its shape and is insertable into the receptacle, said liner having a concave bottom wall and integral laterally spaced apart side walls for generally conforming to the U-shaped space in the receptacle and for accommodating the head therein, shape and is insertable into the receptacle, said liner having a concave bottom wall and integral laterally spaced apart side walls for generally conforming to the U-shaped space in the receptacle and for accommodating the head therein.

2. The holder according to claim 1 wherein said liner is composed of foam that is flexible enough to conform to the shape of the head of the subject and rigid enough to maintain its shape.

3. The holder according to claim 1 wherein there is an opening in each of the side walls of said liner for accommodating the ears of the subject.

4. The holder according to claim 1 wherein there is an opening in each of the side walls of said liner for accommodating the ears of said subject and there are holes in said head restraint sheet for registering with said openings, respectively, to allow for passage of sound to the ears of the subject.

5. The holder according to claim 1 wherein there is an open topped notch in the upper edge of each of the side walls comprising said liner for accommodating the ears of said subject and for permitting sound to pass through the notches to the ears of the subject.

6. The holder according to any one of claims 1, 2, 3, 4 or 5 including pile material fastened to the outside of said rigid U-shaped receptacle and hook material fastened to said free ends of said head restraint straps whereby when the free ends of the straps are wrapped over the head of the subject while the head is in said liner and the liner is in said head restraint means said hook and pile materials are engageable to stabilize the head relative to the receptacle.

7. The holder according to claim 1 including a longitudinally tapered wedge for being inserted in said receptacle to tilt the head of the subject.

8. The holder according to claim 1 including a plurality of longitudinally tapered wedges having different angles of taper, a selected one of said wedges being insertable in said receptacle in either of the two longitudinally opposite directions to tilt the head forward or backward.

9. The holder according to claim 1 including a wedge that is tapered in the longitudinal direction on one side and is curved in the lateral direction for being inserted in the receptacle to tilt the head of the subject either forward or backward, the curvature of said wedge conforming substantially to the curvature of the concave bottom wall of said receptacle.

10. The holder according to any of claims 7, 8 or 9 wherein said wedge or wedges consist of a slightly resilient closed-cell foam material.

11. The holder according to any one of claims 7, 8 or 9 wherein said wedge has a taper in the range of about 10° to about 25°.

12. The head holder according to claim 6 including a chin strap for restraining the chin of a subject whose head is in the receptacle, said chin strap having free ends and hook material fastened to said ends whereby when said chin strap is laid over the chin the hook material at the free ends of the strap can be engaged with the pile material on said receptacle to thereby impose a restraining force on the chin.

13. The chin strap according to claim 11 in which there is a hole in the strap between its free ends such that the tip of the chin may enter the hole to thereby improve the restraint.

14. A head holder for stabilizing the head of a subject lying on a body supporting cradle, the holder comprising:
    a preformed U-shaped member comprised of a longitudinally extending concave bottom wall and laterally spaced apart side walls projecting, respectively, from opposite sides of the bottom wall whereby to define an inside space for containing the head of the subject, said member being composed of X-ray transmissive resilient foam material having sufficient durometer for said member to maintain its preformed shape when it is not subjected to external forces,
    head restraint means comprised of a sheet of X-ray transmissive material that is generally conforming to the contour of the outside of said preformed foam U-shaped member,
    a strap fastened intermediate of its ends to said head restraint means to enable wrapping said strap across the front of the head of the subject that is positioned in said resilient U-shaped foam member, and means for fastening the ends of the strap to said cradle.

15. The head holder according to claim 14 wherein the means for fastening the ends of the strap to the cradle comprise hook material attached to said strap ends for being engaged with pile material that is attached to said cradle.

* * * * *